United States Patent

Breyne et al.

(10) Patent No.: US 6,506,322 B1
(45) Date of Patent: Jan. 14, 2003

(54) NAPHTHOPYRANS ANNELATED IN $C_5$-$C_6$ WITH AN INDENE- OR DIHYDRONAPHTHALENE-TYPE CARBOCYCLE, AND COMPOSITIONS AND (CO)POLYMER MATRICES CONTAINING THEM

(75) Inventors: Olivier Breyne, Lyons (FR); You-Ping Chan, Lyons (FR); Patrick Jean, Lyons (FR)

(73) Assignee: Corning Incorporated, Corning, NY (US)

(*) Notice: Subject to any disclaimer, the term of this patent is extended or adjusted under 35 U.S.C. 154(b) by 69 days.

(21) Appl. No.: 09/712,058

(22) Filed: Nov. 14, 2000

(30) Foreign Application Priority Data

Nov. 17, 1999 (FR) .............................. 99 14425

(51) Int. Cl.⁷ .......................... G02B 5/23; C07D 311/78
(52) U.S. Cl. ....................... 252/586; 549/382; 549/381; 549/331; 524/110; 540/596; 546/196; 548/525
(58) Field of Search .................. 252/586; 549/382, 549/331, 381; 524/110; 540/596; 546/196; 548/525

(56) References Cited

U.S. PATENT DOCUMENTS

| | | | |
|---|---|---|---|
| 3,567,605 A | 3/1971 | Becker | 204/158 |
| 3,627,690 A | 12/1971 | Casella et al. | 252/300 |
| 4,826,977 A | 5/1989 | Heller et al. | 544/70 |
| 5,200,116 A | 4/1993 | Heller | 252/586 |
| 5,238,981 A | 8/1993 | Knowles | 524/110 |
| 5,411,679 A | 5/1995 | Kumar | 252/586 |
| 5,429,774 A | 7/1995 | Kumar | 252/586 |
| 5,451,344 A | 9/1995 | Knowles | 252/586 |
| 5,548,814 A | 8/1996 | Lorang | 455/38 |
| 5,645,767 A | 7/1997 | Van Gemert | 252/586 |
| 5,651,923 A | 7/1997 | Kumar | 252/586 |
| 5,698,141 A | 12/1997 | Kumar | 252/586 |
| 5,783,116 A | 7/1998 | Lin | 252/586 |
| 5,869,658 A | 2/1999 | Lin et al. | 544/106 |
| 6,146,554 A | * 11/2000 | Melzig et al. | 252/586 |
| 6,149,841 A | * 11/2000 | Kumar | 252/586 |
| 6,296,785 B1 | * 10/2001 | Nelson et al. | 252/586 |
| 6,315,928 B1 | * 11/2001 | Mann et al. | 252/586 |
| 6,340,765 B1 | * 1/2002 | Momoda et al. | 549/331 |
| 2001/0025948 A1 | * 10/2001 | Walters et al. | 252/586 |

FOREIGN PATENT DOCUMENTS

| | | |
|---|---|---|
| EP | 0 562 915 B1 | 7/2000 |
| FR | 2762845 | 11/1998 |
| WO | WO-A-94 22850 | 10/1994 |
| WO | WO-A-95 05382 | 2/1995 |
| WO | WO-A-95 27716 | 10/1995 |
| WO | WO-A-96 14596 | 5/1996 |
| WO | WO-A-97 21698 | 6/1997 |
| WO | WO-A-99 31082 | 6/1999 |

OTHER PUBLICATIONS

Edens et al., Mechanism of the Meyer–Schuster Rearrangement, J. Org. Chem., vol. 42, No. 21, 1977, pp. 3403–3408.
Crano et al., Spiroxazines and their use in photochromic lenses, Applied Photochromic Polymer Systems, Chapter 2, 1992, pp. 30–79.

* cited by examiner

Primary Examiner—Philip Tucker
(74) Attorney, Agent, or Firm—Peter Rogalskyj; Angela N. Nwaneri

(57) ABSTRACT

The present invention relates to novel naphthopyran-type compounds, annelated in position $C_5$–$C_6$ by an indene- or dihydronaphthalene-type carbocycle, which are of the formulae (I) and (II) given below:

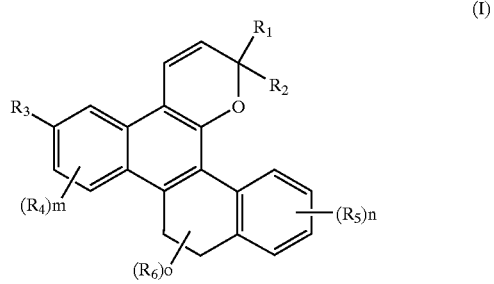

(I)

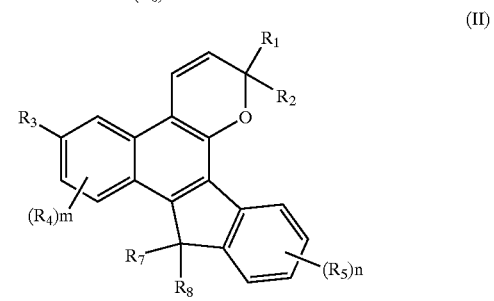

(II)

These compounds (I) and (II) have interesting photochromic properties. The invention also relates to their preparation, to their applications as photochromes, as well as to the compositions and (co)polymer matrices containing them.

26 Claims, No Drawings

NAPHTHOPYRANS ANNELATED IN $C_5$-$C_6$ WITH AN INDENE- OR DIHYDRONAPHTHALENE-TYPE CARBOCYCLE, AND COMPOSITIONS AND (CO)POLYMER MATRICES CONTAINING THEM

This application claims the benefit of priority of FR Application No. 99 14425, filed Nov. 17, 1999, entitled Naphthopyrans Annelated In $C_5$–$C_6$ With An Indene- Or Dihydronaphthalene-Type Carbocycle, And Compositions And (Co)Polymer Matrices Containing Them, of Breyne et al.

The present invention relates to novel naphthopyran-type compounds which are annelated in $C_5$–$C_6$ with an indene- or dihydronaphthalene-type carbocycle, and which have, in particular, photochromic properties. The invention also relates to photochromic compositions and photochromic ophthalmic articles (lenses for example) which contain said naphthopyrans. The invention also covers the preparation of these novel compounds.

The photochromic compounds are capable of changing colour under the influence of a poly- or mono-chromatic light (UV for example) and of returning to their initial colour when the luminous irradiation ceases, or under the influence of temperature and/or a poly- or mono-chromatic light different from the first.

The photochromic compounds find applications in various fields, e.g. for the manufacture of ophthalmic lenses, contact lenses, solar protection glasses, filters, camera optics or photographic apparatus optics or other optical devices and observation devices, glazing, decorative objects, bill elements or even for information storage by optical inscription (coding).

In the field of ophthalmic optics, and in particular the spectacles trade, a photochromic lens which comprises one or more photochromic compounds must have:
- a high transmission in the absence of ultraviolets,
- a low transmission (high colourability) under solar irradiation,
- adapted coloration and discoloration kinetics,
- a tint acceptable to the consumer (grey or brown preferably) with preferably a maintenance of the chosen tint during the coloration and the discoloration of the lens,
- a maintenance of the performances, the properties, within a temperature range of 0–40° C.,
- a significant durability, since these objectives sought after are sophisticated corrective lenses and therefore expensive.

These lens characteristics are in fact determined by the active photochromic compounds which they contain; compounds which must furthermore be perfectly compatible with the organic or inorganic, even hybrid support which constitutes the lens.

Moreover, it is to be noted that obtaining a grey or brown tint may necessitate the use of at least two photochromes of different colours, i.e. having distinct maximal absorption wavelengths in the visible. This combination further imposes other requirements of the photochromic compounds. In particular, the coloration and discoloration kinetics of the (two or more) combined active photochromic compounds must be essentially identical. The same applies for their stability with time and also for their compatibility with a plastic, inorganic or organic-inorganic hybrid support.

Amongst the numerous photochromic compounds described in the prior art, benzopyrans and naphthopyrans may be cited which are described in patents or patent applications: U.S. Pat. No. 3,567,605, U.S. Pat. No. 3,627,690, U.S. Pat. No. 4,826,977, U.S. Pat. No. 5,200,116, U.S. Pat. No. 5,238,981, U.S. Pat. No. 5,411,679, U.S. Pat. No. 5,429,744, U.S. Pat. No. 5,451,344, U.S. Pat. No. 5,458,814, U.S. Pat. No. 5,651,923, U.S. Pat. No. 5,645,767, U.S. Pat. No. 5,698,141, U.S. Pat. No. 5,783,116, WO-A-95 05382, FR-A-2,718,447, WO-A-96 14596, WO-A-97 21698, which are of the reduced formulae below:

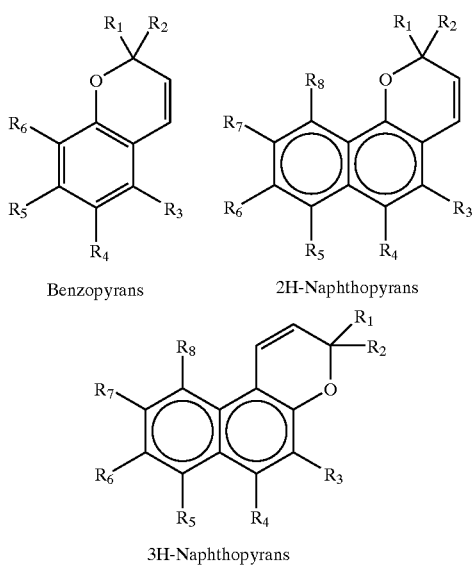

Benzopyrans           2H-Naphthopyrans

3H-Naphthopyrans

In particular, patent documents WO-A-99 31082 and U.S. Pat. No. 5,869,658 claim 3H-naphthopyran-type structures in which there exists an aryl group in $R_4$:

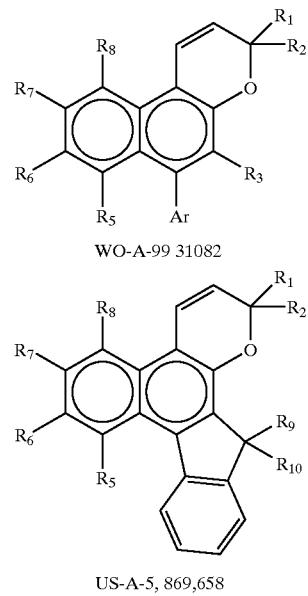

WO-A-99 31082

US-A-5, 869,658

These compounds claim to satisfy the specifications defined above. In reality, if these compounds really do have one or more of the basic properties sought after, such as a high transmission in the absence of ultraviolets and a high colourability under solar irradiation, none of the compounds described hitherto have the complete combination of the properties sought after which are necessary for the production of satisfactory articles. In particular, none of these compounds is intrinsically grey or brown and the necessity of using an additional photochrome in order to obtain one of these two tints does subsist.

In this context, it is to the credit of the inventors for having been interested in this type of derivative as a base for developing novel photochromes, and for having proposed a novel family of molecules which have particularly advantageous photochromic properties.

Thus, according to a first of its aspects, the present invention relates to compounds of formulae (I) and (II):

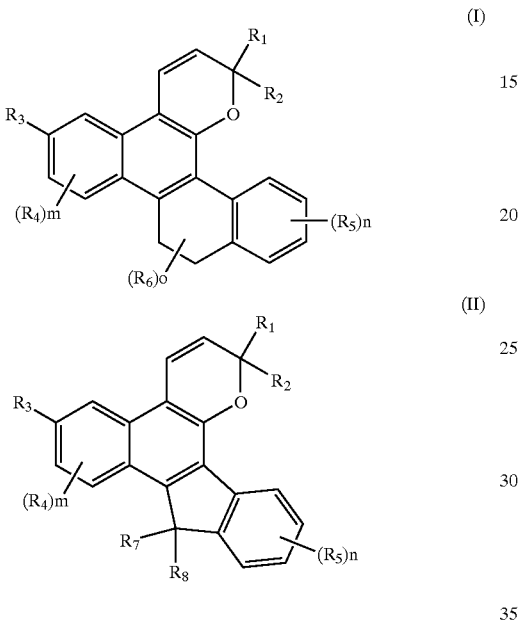

in which:

$R_1$ and $R_2$, which are identical or different, independently represent:
hydrogen,
a linear or branched alkyl group comprising 1 to 12 carbon atoms,
a cycloalkyl group comprising 3 to 12 carbon atoms,
an aryl or heteroaryl group comprising in its basic structure 6 to 24 carbon atoms or 4 to 24 carbon atoms respectively and at least one heteroatom selected from sulphur, oxygen and nitrogen; said basic structure being optionally substituted with at least one substituent selected from the whole of the substituents given below:
  a halogen, and notably fluorine, chlorine and bromine,
  a hydroxy,
  a linear or branched alkyl group comprising 1 to 12 carbon atoms,
  a linear or branched alkoxy group comprising 1 to 12 carbon atoms,
  a haloalkyl or haloalkoxy group corresponding to the ($C_1$–$C_{12}$) alkyl or alkoxy groups above respectively which are substituted with at least one halogen atom, and notably a fluoroalkyl group of this type,
  a phenoxy or naphthoxy group optionally substituted with at least one linear or branched alkyl or alkoxy group comprising 1 to 12 carbon atoms,
  a linear or branched alkenyl group comprising 2 to 12 carbon atoms, and notably a vinyl group or an allyl group,
  an —$NH_2$ group,
  an —NHR group, R representing a linear or branched alkyl group comprising 1 to 6 carbon atoms, or a phenyl group optionally substituted with at least one linear or branched alkyl group comprising 1 to 6 carbon atoms,
  a

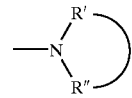

group, R' and R", which are identical or different, representing independently a linear or branched alkyl group comprising 1 to 6 carbon atoms, or a phenyl group optionally substituted with at least one linear or branched alkyl group comprising 1 to 6 carbon atoms, or representing together with the nitrogen atom to which they are bound a 5- to 7-membered ring which can comprise at least one other heteroatom selected from oxygen, sulphur and nitrogen, said nitrogen being optionally substituted with an R''' group, which is a linear or branched alkyl group comprising 1 to 6 carbon atoms,
  a methacryloyl group or an acryloyl group,
  an aralkyl or heteroaralkyl group, the alkyl group of which, which is linear or branched, comprises 1 to 4 carbon atoms and the aryl part of which has the same definition as that given supra for the aryl and heteroaryl group;

or
  said two substituents $R_1$ and $R_2$ together form an adamantyl, norbornyl, fluorenylidene, di($C_1$–$C_6$) alkylanthracenylidene or spiro($C_5$–$C_6$) cycloalkylanthracenylidene group; said group being optionally substituted with at least one of the substituents listed above for $R_1$, $R_2$: an aryl or heteroaryl group;

$R_3$ represents:
  a hydroxy;
  a linear or branched alkoxy group comprising 1 to 6 carbon atoms;
  a

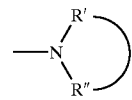

group, R' and R", which are identical or different, representing independently a linear or branched alkyl group comprising 1 to 6 carbon atoms, a phenyl group optionally substituted with at least one linear or branched alkyl group comprising 1 to 6 carbon atoms, or representing together with the nitrogen atom to which they are bound a 5- to 7-membered ring which can comprise at least one other heteroatom selected from oxygen, sulphur and nitrogen, said nitrogen being optionally substituted with an R''' group, which is a linear or branched alkyl group comprising 1 to 6 carbon atoms, $R_4$, which are identical or different, independently represent:
  a halogen, and notably fluorine, chlorine or bromine,
  a hydroxy, a linear or branched alkyl group comprising 1 to 12 carbon atoms (advantageously 1 to 6 carbon atoms),
a cycloalkyl group comprising 3 to 12 carbon atoms,
a linear or branched alkoxy group comprising 1 to 12 carbon atoms (advantageously 1 to 6 carbon atoms),
a haloalkyl, halocycloalkyl, or haloalkoxy group corresponding to the alkyl, cycloalkyl, alkoxy groups above respectively, which are substituted with at least one halogen atom, notably selected from fluorine, chlorine and bromine,
an aryl or heteroaryl group having the same definition as that given supra for $R_1$, $R_2$,
an aralkyl or heteroaralkyl group, the alkyl group, which is linear or branched, comprises 1 to 4 carbon atoms, and the aryl and heteroaryl groups having the same definitions as those given supra for $R_1$, $R_2$,
a phenoxy or naphthoxy group optionally substituted with at least one linear or branched alkyl or alkoxy group comprising 1 to 12 carbon atoms,
an amine or amide group: —$NH_2$, —NHR, —$CONH_2$, —CONHR,

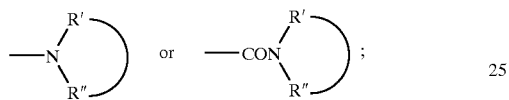

R, R', R" having their respective definitions given supra for the amine substituents of the values $R_1$, $R_2$: aryl or heteroaryl,
an —$OCOR_9$ or —$OCOOR_9$ group, $R_9$ representing a linear or branched alkyl group comprising 1 to 6 carbon atoms, or a cycloalkyl group comprising 3 to 6 carbon atoms, or a phenyl group, optionally substituted with at least one of the substituents listed above for the values of $R_1$, $R_2$: aryl or heteroaryl;

$R_5$, which are identical or different, represent the substituents listed above for the values of $R_4$, or
at least two of the adjacent $R_5$ groups together form an aromatic or non-aromatic cyclic group having one or two annelated rings which can comprise at least one heteroatom selected from the group consisting of: oxygen, sulphur or nitrogen; this or these rings, independently 5- to 7-membered aromatic or non-aromatic, being able to comprise at least one substituent selected from a group as defined above, as a substituent, of the basic structure of the aryl or heteroaryl group representing $R_1$ or $R_2$;

$R_6$, which are identical or different, independently represent a linear or branched alkyl group comprising 1 to 6 carbon atoms;

$R_7$ and $R_8$, which are identical or different, independently represent a hydrogen or a linear or branched alkyl group comprising 1 to 6 carbon atoms, or
one of them represents a hydrogen or a linear or branched alkyl group comprising 1 to 6 carbon atoms whereas the other is selected from a hydroxy group, a linear or branched alkoxy group comprising 1 to 6 carbon atoms, a —$OCOR_9$ or a —$OCOOR_9$ group, $R_9$ representing a linear or branched alkyl group comprising 1 to 6 carbon atoms or a cycloalkyl group comprising 3 to 6 carbon atoms or a phenyl group, optionally substituted with at least one of the substituents listed above for the values of $R_1$, $R_2$: aryl or heteroaryl, or
$R_7$ and $R_8$ together form an oxo group or a cycloalkyl group comprising 3 to 6 carbon atoms;

m is an integer from 0 to 3 and n and o are integers from 0 to 4.

The person skilled in the art will obviously have understood that the branched alkyl, alkoxy and alkenyl groups, as defined above, comprise a sufficient number of carbons in order to be branched (i.e. more than 3, more than 3, and more than 4 carbon atoms respectively).

The compounds of the invention—annelated naphthopyrans of formulae (I) and (II)—have very fast discoloration kinetics combined with a high colourability.

Amongst said compounds of the invention, preferred are those which have the formulae (I) and/or (II) in which:

$R_1$, $R_2$ are identical or different and represent independently optionally substituted aryl or heteroaryl groups the basic structure of which is selected from the group comprising phenyl, naphthyl, biphenyl, pyridyl, furyl, benzofuryl, dibenzofuryl, N—($C_1$–$C_6$)alkylcarbazole, thienyl, benzothienyl, dibenzothienyl and julolidinyl groups; $R_1$ and/or $R_2$ representing, advantageously, a para-substituted phenyl group;

or
$R_1$ and $R_2$ together form an adamantyl or norbornyl group;

$R_4$ and $R_5$ represent a halogen, an alkyl group or an alkoxy group;

$R_7$ represents a hydroxy or an alkyl group and $R_8$ represents a hydrogen or an alkyl group;

m and n=1 and o=0.

According to a second of its aspects, the present invention relates to a method of preparation of the compounds (I) and (II), characterised in that it comprises condensing:

an intermediate product of formula (III) or (IV) which are given below:

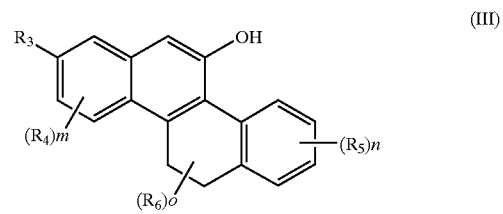

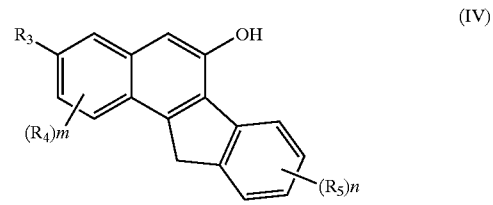

in which $R_3$, $R_4$, $R_5$, $R_6$, m, n and o are as defined supra with reference to formulae (I) and (II);

with a derivative of propargylic alcohol, having formula (V) below:

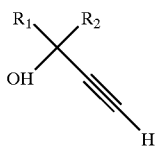

(V)

in which $R_1$ and $R_2$ are as defined supra with reference to formulae (I) and (II);

the condensation (III) or (IV)/(V) being carried out advantageously in the presence of a catalyst, this catalyst being preferably selected from the group comprising para-toluenesulphonic acid, dodecylsulphonic acid or bromoacetic acid;

or with an aldehyde derivative, having formula (V') below:

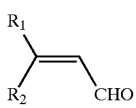

(V')

in which $R_1$ and $R_2$ are as defined supra with reference to formulae (I) and (II);

the condensation (III) or (IV)/(V') being carried out, advantageously, in the presence of a metallic complex, preferably a complex of titanium, titanium (IV) ethoxide being particularly preferred.

In practice, the condensation reaction between compounds (III) or (IV) and (V) or (V') can take place in solvents such as toluene, xylene or tetrahydrofuran, to which appropriate catalysts are optionally added. For more details on the condensation of compounds (III) or (IV)/(V'), reference may be made to the EP-A-0 562 915 patent application.

The compounds of formula (V) are known to the person skilled in the art and are obtained from the corresponding ketone according to a method described notably in the WO-A-96 14596 patent application. The ketone is itself commercial or is prepared according to the known methods such as the Friedel Crafts method (cf WO-A-96 14596 and cited references).

Aldehydes (V'), which are derivatives of (V), are obtained by rearrangement in an acid medium (cf *J. Org. Chem.*, 1977, 42, 3403).

In the case of the compounds of formula II, the condensation of the compounds of formula IV with compounds of formula V or V' leads to the intermediate IIa (compound of formula (II) in which $R_7=R_8=H$) which can be derivatised, notably in the following manner:

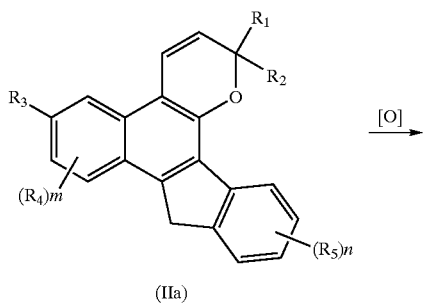

(IIa)

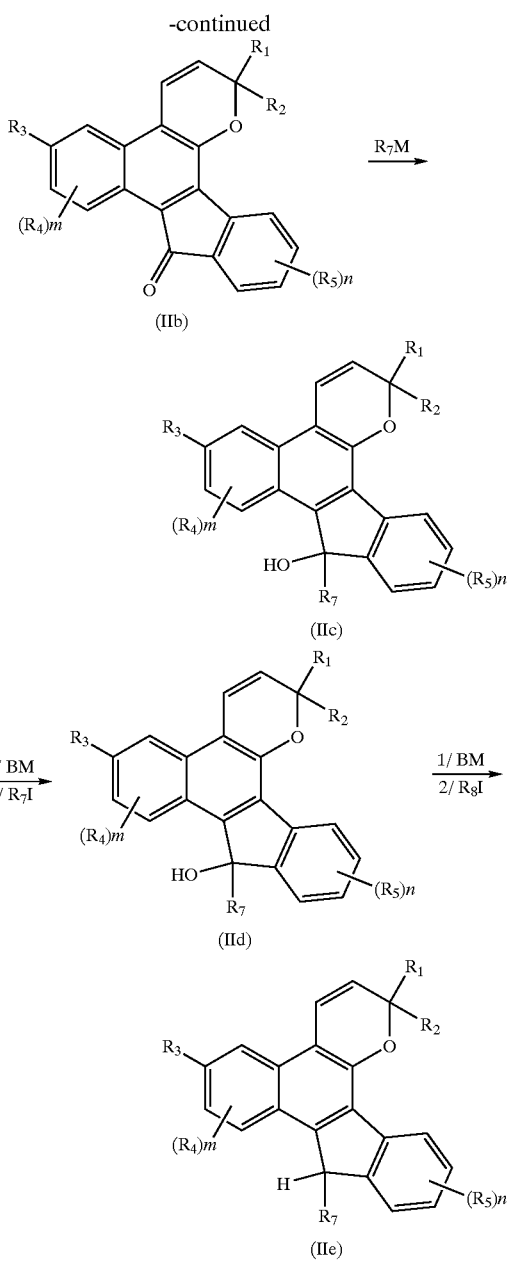

The oxidation in the air of the compounds (IIa) in the presence of a basic PTC such as benzyltrimethylammonium hydroxide leads to compounds (IIb) which are hydroxyalkylated by organometallic reagents such as methyllithium in order to provide compounds (IIc).

Alternatively, compounds (IIa) can be alkylated by metallation with a base such as butyllithium, and then reaction with an alkyl iodide such as $CH_3I$ in order to provide compounds (IId) and then compounds (IIe).

The preparation of the other compounds of formula (II) is within reach of the person skilled in the art. For all intents and purposes, it may still be indicated in a non-limiting way:

that the compounds of formula (II) in which $R_7+R_8=$ cycloalkyl can be prepared from the corresponding compounds of formula (IId) above in which "$R_7$" is an alkyl functionalised with a leaving group. Said "compounds of formula (IId)" are subjected to an intramolecular nucleophilic substitution of said leaving group; and that compounds of formula (II) in which $R_7$ or $R_8$=alkoxy, —$OCOR_9$ —$OCOOR_9$ can be obtained in a classical manner from the corresponding compounds of formula (II) in which $R_7$ or $R_8$=OH.

Compounds of formula (III) and (IV) are obtained according to a synthesis scheme, the various steps of which are adaptations of known methods. The preferred general synthesis scheme is given below:

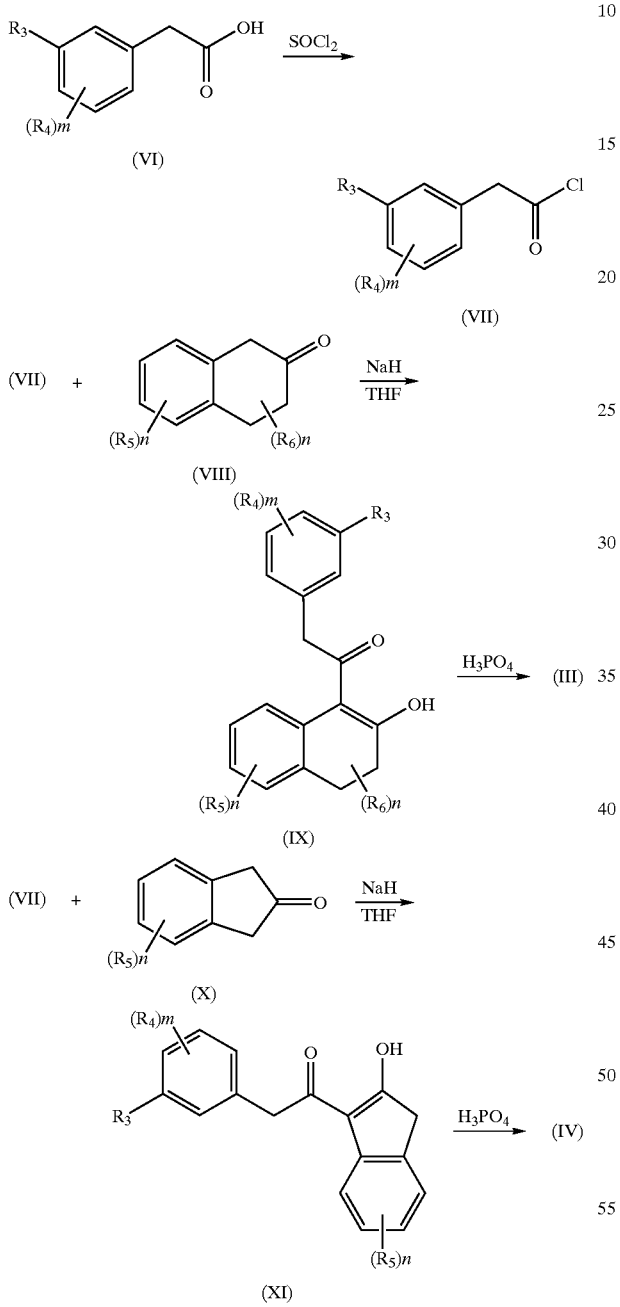

In a first step, acid VI (commercial or prepared according to known methods) is converted into acid chloride VII. The latter chloride is then allowed to condense with a β-tetralone VIII or a β-indanone X in the presence of a large excess of NaH in order to lead to intermediates IX and XI which are cyclised to give III and IV, respectively, by heating in the presence of an acid such as phosphoric acid.

According to a third of its aspects, the invention also relates to the novel intermediate products of formulae (III) and (IV), recalled below:

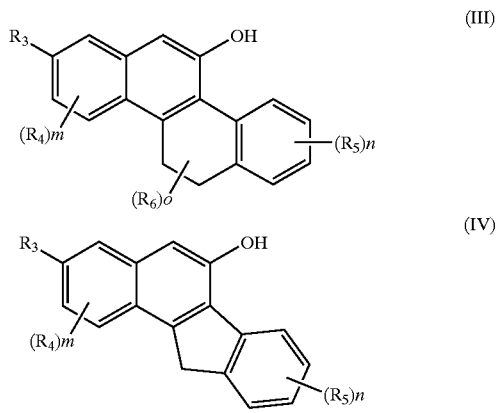

in which $R_3$, $R_4$, $R_5$, $R_6$, m, n and o are as defined above with reference to formulae (I) and (II).

According to a fourth of its aspects, the object of the invention is (co)polymer(s) and/or reticulate(s) obtained by polymerising and/or cross-linking and/or grafting at least one compound (I) or (II) as defined above. The compounds (I) and (II) according to the invention can be per se (co) monomers and/or be comprised in (co)polymerisable and/or cross-linkable (co)monomers. The (co)polymers and/or reticulates thus obtained can constitute photochromic matrices such as those presented infra.

According to a fifth of its aspects, the present invention relates to the use of said compounds of formula (I) or (II) of the invention as photochromic agents. Another object of the invention is, therefore:

firstly, novel photochromic compounds which are constituted by the $C_5$–$C_6$-annelated naphthopyran derivatives such as defined above, taken alone or in a mixture of themselves and/or with at least one other photochromic compound of another type and/or with at least one non-photochromic colouring agent;

secondly, novel photochromic compositions which comprise at least one compound (I) or (II) as defined above, and/or at least one linear or cross-linked (co)polymer containing at least one compound (I) or (II) according to the invention in its structure. Such photochromic compositions can contain at least one other photochromic compound, of another type and/or at least one non-photochromic colouring agent and/or at least one stabilising agent. These photochromic compounds of another type, non-photochromic colouring agents, and stabilising agents are prior art products known to the person skilled in the art.

Within the context of the present invention, combinations of photochromic compounds of the invention and/or combinations of photochromic compounds of the invention and photochromic compounds of another type according to the prior art are particularly recommended; such combinations being interesting in that they are suitable for generating grey or brown tints, which are desired by the public in applications such as ophthalmic spectacles or solar spectacles.

These additional photochromic compounds can be those known to the person skilled in the art and described in the literature, e.g. chromenes (U.S. Pat. No. 3,567,605, U.S. Pat. No. 5,238,981, WO-A-94 22850, EP-A-0 562 915), spiropyrans or naphthospiropyrans (U.S. Pat. No. 5,238,981) and spiroxazines (Crano et al., "Applied Photochromic Polymer Systems", Ed. Blackie & Son Ltd, 1992, chapter 2).

Said compositions according to the invention can also comprise:

non-photochromic colouring agents which enable adjusting the tint, and/or one or more stabilising agents, such as an anti-oxidising agent for example, and/or one or more anti-UV, and/or one or more anti-radicals, and/or one or more photochimic excited state deactivators.

These additives can notably enable improving the durability of said compositions.

The compounds of the invention envisaged within the context of their photochromic applications can be used in solution. Thus, a photochromic solution can be obtained by dissolving at least one of said compounds in an organic solvent such as toluene, dichloromethane, tetrahydrofuran or ethanol. The solutions obtained are in general colourless and transparent. When exposed to sunlight, they develop a strong coloration and regain the colourless state when they are placed in an area of less exposure to the sun's rays or, in other words, when they are no longer submitted to UV. In general, a very low concentration of product (of the order of 0.01 to 5% by weight) is sufficient to obtain an intense coloration.

The compounds according to the invention are furthermore compatible with support matrices of organic polymer or of inorganic material (even of an inorganic-organic hybrid material), in a form included in said matrices as well as in the form of a coating of said matrices.

photochrome, in a silicone oil, in an aliphatic or aromatic hydrocarbon, or in a glycol, or from another polymer matrix, can be cited for example. The diffusion is commonly carried out at a temperature of 50 to 200° C. for a period of time of 15 minutes to several hours, according to the nature of the polymer matrix. Another implementation technique consists in mixing the photochrome in a formulation of polymerisable materials, depositing this mixture on a surface or in a mould, and then carrying out the copolymerisation. These implementation techniques, and others, are described in the article by Crano et al. "Spiroxazines and their use in photochromic lenses" published in Applied Photochromic Polymer Systems, Ed. Blackie and Son Ltd—1992.

The following products may be mentioned as examples of preferred polymer materials for forming matrices which are useful in optical applications of the photochromic compounds according to the invention:

alkyl, cycloalkyl, (poly or oligo)ethylene glycol, aryl or arylalkyl mono-, di- tri- or tetraacrylate or mono-, di-, tri- or tetramethacrylate, which is optionally halogenated or which comprises at least one ether and/or ester and/or carbonate and/or carbamate and/or thiocarbamate and/or urea and/or amide group, polystyrene, polyether, polyester, polycarbonate (e.g. bisphenol-A polycarbonate, diallyl diethylene glycol polycarbonate), polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate or polyvinylbutyral, those obtained from difunctional monomers having the formula below:

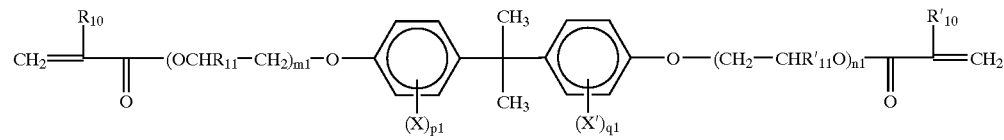

Also, within the context of the fifth aspect of the invention in relation to the photochromic applications, the object of the invention is a matrix which comprises:

at least one compound (I) or (II), as defined supra;

and/or at least one (co)polymer and/or reticulate, as defined supra;

and/or at least one composition, as presented above.

The most interesting applications of the compounds of the invention are in fact those in which the photochrome is dispersed uniformly within or on the surface of a matrix formed by a polymer and/or copolymer and/or mixture of (co)polymers.

Following the example of their behaviour in solution, the compounds (I) or (II), included in a polymer matrix are colourless or slightly coloured in the initial state and rapidly develop an intense coloration under a UV light (365 nm) or under a light source of the solar type. Finally, they regain their initial coloration once the irradiation ceases.

The methods of implementation which can be envisaged in order to obtain such a matrix are very varied. Amongst those known to the person skilled in the art, the diffusion in the (co)polymer, from a suspension or solution of the in which:

$R_{10}$, $R'_{10}$, $R_{11}$, and $R'_{11}$ are identical or different and represent independently a hydrogen or a methyl group;

$m_1$ and $n_1$ are, independently, integers between 0 and 4 (inclusive); and are advantageously independently equal to 1 or 2;

X and X', which are identical or different, are a halogen and represent, preferably, a chlorine and/or a bromine;

$p_1$ and $q_1$ are, independently, integers between 0 and 4 (inclusive);

copolymers of at least two types of copolymerisable monomers selected from the precursor monomers of the polymers listed supra, and preferably those belonging to the groups comprising (meth)acrylic monomers, vinylic monomers, allylic monomers, and mixtures thereof.

In a particularly preferred manner, the photochromes of the invention are used with resins which have a nanobiphasic structure and which are obtained by copolymerising at least two different, specific difunctional monomers. Such resins have been described by the Applicant in the French patent Application FR-A-2,762,845.

The amount of photochrome used in the (co)polymer matrix depends upon the degree of darkening desired. Usually, between 0.001 and 20% by weight of it is used.

Still according to the fifth of its aspects in relation to the applications of the compounds (I) or (II) as photochromes, another object of the present invention is ophthalmic articles, such as ophthalmic or solar spectacle articles, comprising:

at least one compound (I) or (II) according to the invention, and/or at least one (co)polymer and/or reticulate formed, at least in part, from compound(s) of the invention, and/or at least one photochromic composition as defined above, and/or at least one matrix (as defined supra), of an organic polymer material or of an inorganic material, or even of a hybrid inorganic-organic material, said matrix initially comprising at least one compound of the invention.

In practice, the articles which are more particularly covered by the present invention are ophthalmic lenses or photochromic solar lenses, glazing (windows for buildings, for locomotion engines, automobile vehicles), optical devices, decorative articles, solar protection articles, information storage, The present invention is illustrated by the Examples which follow, of synthesis and of photochromic validation, of compounds of the invention. This compound of the invention is compared to prior art compound C5.

EXAMPLES

Example 1

Synthesis of Compound (C1)

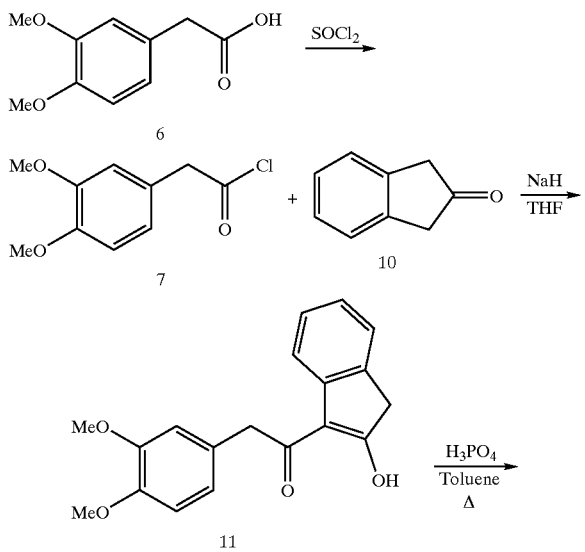

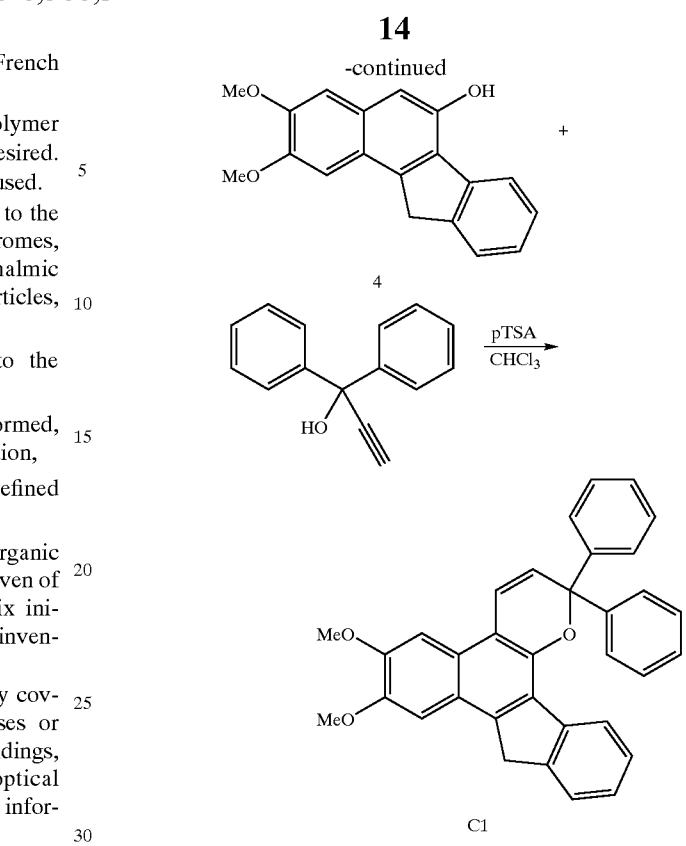

Step 1:
Thionyl chloride (16 ml) is allowed to react with homoveratric acid 6 (19.6 g) in dichloromethane (100 ml) in the presence of a catalytic amount of DMF (0.5 ml). Stirring is effected under reflux for 4 h. The solvent is then evaporated off to provide 22.7 g of acid chloride 7 (yellow oil).

Step 2:
NaH (800 mg of a 60% suspension in mineral oil) is cautiously added in portions to a solution of 7 (2.14 g) and 2-indanone 10 (1.32 g) in THF (15 ml). Stirring is effected under reflux for 1 h, and then 0.4 g of sodium hydride are added. Stirring is continued for 1 h, and the mixture is then hydrolysed with a 1N solution of HCl. After extraction and evaporation of the solvents, the reaction mixture is purified by silica column chromatography to provide compound 11 (1.04 g, yellow powder).

Step 3:
15 ml of an 85% aqueous solution of phosphoric acid are added to a solution of 11 (2.5 g) in toluene (30 ml). The water present in the medium is distilled off with the aid of a Dean-Stark apparatus. Stirring is effected under reflux for 5 h. The mixture is cooled, water is added, and the precipitate of naphthol 4 (800 mg dry, beige solid) is filtered off.

Step 4:
A few crystals of pTSA (para-toluenesulphonic acid) are added to a solution of 400 mg of naphthol 4 and 370 mg of 1,1-diphenylpropyn-1-ol in 10 ml of chloroform. Stirring under reflux is effected for 1 h. The reaction mixture is then purified by filtration over silica. The solid obtained is recrystallised to provide 160 mg of slightly pink crystals which are pure by $^1$H NMR.

Example 2

Synthesis of Compound (C2)

Step 1:
0.5 ml of a 40% by weight solution of benzyltrimethylammonium hydroxide is added to a solution of compound C1 (160 mg) in 15 ml of THF. Reaction is allowed with air for 2 h, and the mixture is poured into H₂O and is acidified with 1N HCl solution. The precipitate is filtered off and recrystallised to provide 110 mg of orange crystals.

Step 2

1 ml of a 1M solution of methyllithium are added at 0° C. to a solution of 190 mg of the product of step 1 in 10 ml of THF. Reaction is allowed for 10 min, and 0.5 ml of methyllithium are then added. After stirring for 10 min at 0° C., the mixture is hydrolysed with a 1N HCl solution and is extracted with ethyl acetate. After evaporation of the solvent, the reaction mixture is purified over silica, and the recrystallised to provide 110 mg of yellow crystals, correct by $^1$H NMR.

Example 3

Synthesis of Compound (C3)

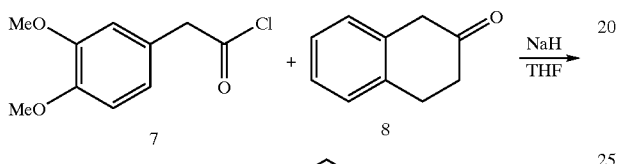

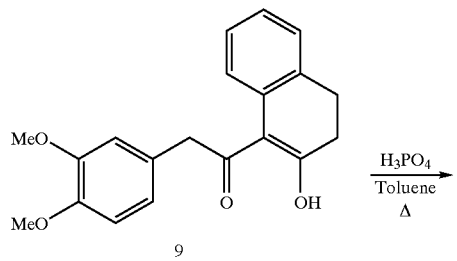

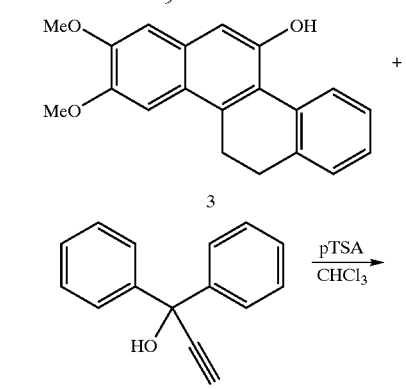

Step 1:

This step is analogous to step 1 of Example 1. 18.5 g of a yellow oil are obtained from 16.1 g of homoveratric acid 6 and 4.1 ml of thionyl chloride.

Step 2:

5.47 g of a white solid, which is in accordance with the desired product 9 by $^1$H RMN, are obtained according to a method which is analogous to that of step 2 of Example 1, from 7.67 g of 2-tetralone 8, 8.21 g of NaH and the product of step 1, Step 3:

2.05 g of a slightly yellow solid are obtained according to a method which is analogous to that of step 3 of Example 1, from 3 g of the product of step 2.

Step 4:

A few crystals of pTSA are added to a solution of 1 g of the product of step 3 and 889 mg of 1,1-diphenylpropyn-1-ol in 100 ml of chloroform. Stirring is effected under reflux for 4 h. The mixture is cooled, and purified by filtration over silica to provide 513 mg of an orange solid, correct by $^1$H NMR.

Example 4

Synthesis of Compound (C4)

A few crystals of pTSA are added to a solution of 470 mg of the product of step 3 of Example 3 and 554 mg of 1,1-bis(p-methoxyphenyl)-propyn-1-ol in 50 ml of chloroform. Stirring under reflux is effected for 4 h. The mixture is cooled, and purified by filtration over silica to provide 509 mg of a pink solid, correct by $^1$H NMR.

Example 5

Compound (C5) of the Prior Art (U.S. Pat. No. 3,567,605).

The photochromic properties of said compounds (C1), (C2), (C3), (C4) and (C5) were evaluated.

Said compounds are dissolved at the rate of 5 mg in 50 ml of THF. The UV-visible absorptions (optical path of 1 cm) are then measured before and after exposure to a 365 nm UV source. The observation of the tints and intensities developed is made by placing the solutions in the sun or before a solar simulator. The properties of these compounds are given in the Table below.

| COMPOUND | STRUCTURE | λ VIS* | T$_{1/2}$** |
|---|---|---|---|
| (C1) | 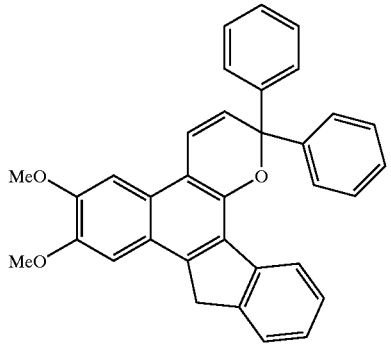 | 434 nm | 10 s |
| (C2) | 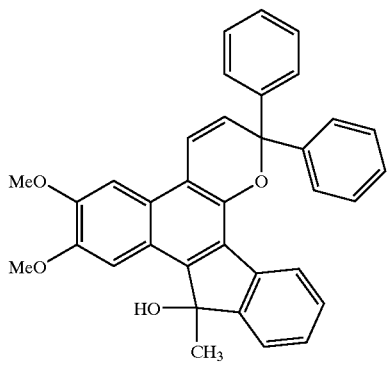 | 442 nm | 5 s |
| (C3) | 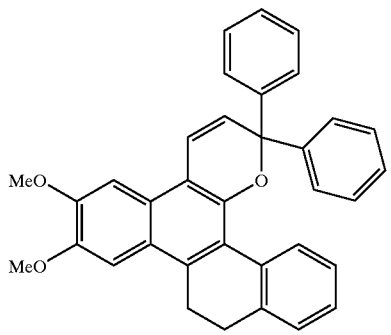 | 428 nm | 63 s |
| (C4) | 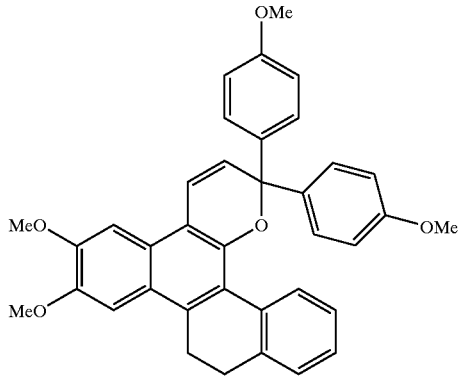 | 458 nm | 12 s |

-continued

| COMPOUND | STRUCTURE | λ VIS* | $T_{1/2}$** |
|---|---|---|---|
| (C5) | 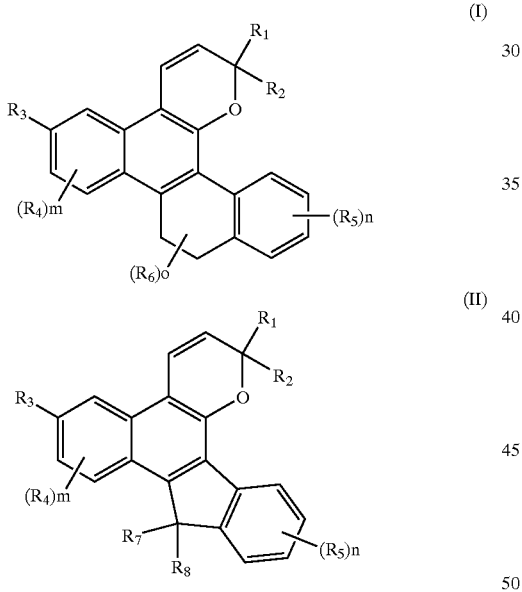 | 428 nm | 11 s |

*λ$_{vis}$ of the band of the highest intensity in the range of the visible spectrum of the compound after exposure.
**decoloration time corresponding to 50% decrease of absorption at the λvis at ambient temperature.

The observation of the solutions in the presence of sun's rays or UV rays shows that the compounds of the invention have a high colourability, notably in comparison with compound (C5).

What is claimed is:

1. A compound having one of the following formulae (I) and (II):

(I)

(II)

in which:
$R_1$, and $R_2$, which are identical or different, independently represent:
hydrogen,
a linear or branched alkyl group comprising 1 to 12 carbon atoms,
a cycloalkyl group comprising 3 to 12 carbon atoms,
an aryl group comprising in its basic structure 6 to 24 carbon atoms or a heteroaryl group comprising in its basic structure 4 to 24 carbon atoms and at least one heteroatom selected from sulphur, oxygen and nitrogen, said aryl or heteroaryl group's basic structure being optionally substituted with at least one substituent selected from the group consisting of:
a halogen,
a hydroxy,
a linear or branched alkyl group comprising 1 to 12 carbon atoms,
a linear or branched alkoxy group comprising 1 to 12 carbon atoms,
a haloalkyl or haloalkoxy group corresponding to the ($C_1$–$C_{12}$) alkyl or alkoxy groups above respectively which are substituted with at least one halogen atom,
a phenoxy or naphthoxy group optionally substituted with at least one linear or branched alkyl or alkoxy group comprising 1 to 12 carbon atoms,
a linear or branched alkenyl group comprising 2 to 12 carbon atoms,
an —$NH_2$ group,
an —NHR group, R representing a linear or branched alkyl group comprising 1 to 6 carbon atoms, or a phenyl group optionally substituted with at least one linear or branched alkyl group comprising 1 to 6 carbon atoms,
a

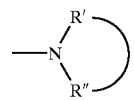

group, wherein R' and R", which are identical or different, independently represent a linear or branched alkyl group comprising 1 to 6 carbon atoms or a phenyl group optionally substituted with at least one linear or branched alkyl group comprising 1 to 6 carbon atoms or wherein R' and R' represent together with the nitrogen atom to which they are bound a 5- to 7-membered ring which optionally comprises at least one other heteroatom selected from oxygen, sulphur, and nitrogen, said nitrogen being optionally substituted with an R''' group, which is a linear or branched alkyl group comprising 1 to 6 carbon atoms, and
a methacryloyl group or an acryloyl group, or
an aralkyl or heteroaralkyl group, the alkyl part of which is linear or branched, comprises 1 to 4 carbon atoms and the aryl part or heteroaryl part of which has the same definition as that given above for the aryl and heteroaryl group;
or
said two substituents $R_1$ and $R_2$ together form an adamantyl, norbornyl, fluorenylidene, di($C_1$–$C_6$)

alkylanthracenylidene, or spiro ($C_5$–$C_6$) cycloalkylanthracenylidene group, said group being optionally substituted with at least one substituent selected from the group consisting of:
a halogen,
a hydroxy,
a linear or branched alkyl group comprising 1 to 12 carbon atoms,
a linear or branched alkoxy group comprising 1 to 12 carbon atoms,
a haloalkyl or haloalkoxy group corresponding to the ($C_1$–$C_{12}$) alkyl or alkoxy groups above respectively which are substituted with at least one halogen atom,
a phenoxy or naphthoxy group optionally substituted with at least one linear or branched alkyl or alkoxy group comprising 1 to 12 carbon atoms,
a linear or branched alkenyl group comprising 2 to 12 carbon atoms,
an —$NH_2$ group,
an —NHR group, R representing a linear or branched alkyl group comprising 1 to 6 carbon atoms, or a phenyl group optionally substituted with at least one linear or branched alkyl group comprising 1 to 6 carbon atoms,
a

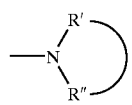

group, wherein R' and R", which are identical or different, independently represent a linear or branched alkyl group comprising 1 to 6 carbon atoms or a phenyl group optionally substituted with at least one linear or branched alkyl group comprising 1 to 6 carbon or wherein R' and R" represent together with the nitrogen atom to which they are bound a 5- to 7-membered ring which optionally comprises at least one other heteroatom selected from oxygen, sulphur, and nitrogen, said nitrogen being optionally substituted with an R'" group, which is a linear or branched alkyl group comprising 1 to 6 carbon atoms, and
a methacryloyl group or an acryloyl group;
$R_3$ represents:
a hydroxy;
a linear or branched alkoxy group comprising 1 to 6 carbon atoms;
a

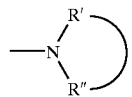

group, wherein R' and R", which are identical or different, independently represent a linear or branched alkyl group comprising 1 to 6 carbon atoms or a phenyl group optionally substituted with at least one linear or branched alkyl group comprising 1 to 6 carbon or wherein R' and R" represent together with the nitrogen atom to which they are bound a 5- to 7-membered ring which optionally comprises at least one other heteroatom selected from oxygen, sulphur, and nitrogen, said nitrogen being optionally substi-
tuted with an R'" group, which is a linear or branched alkyl group comprising 1 to 6 carbon atoms;
$R_4$, which are identical or different, independently represent:
a halogen,
a hydroxy,
a linear or branched alkyl group comprising 1 to 12 carbon atoms,
a cycloalkyl group comprising 3 to 12 carbon atoms,
a linear or branched alkoxy group comprising 1 to 12 carbon atoms,
a haloalkyl, halocycloalkyl, or haloalkoxy group corresponding respectively to the alkyl, cycloalkyl, and alkoxy groups above, which are substituted with at least one halogen atom,
an aryl or heteroaryl group having the same definition as that given above for $R_1$, $R_2$,
an aralkyl or heteroaralkyl group, the alkyl pary of which is linear or branched and comprises 1 to 4 carbon atoms and the aryl or heteroaryl part of which has the same definitions as those given above for $R_1$, $R_2$,
a phenoxy or naphthoxy group optionally substituted with at least one linear or branched alkyl or alkoxy group comprising 1 to 12 carbon atoms,
an amine or amide group: —$NH_2$, —NHR, —$CONH_2$, —CONHR,

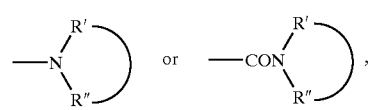

wherein R represents a linear or branched alkyl group comprising 1 to 6 carbon atoms or a phenyl group optionally substituted with at least one linear or branched alkyl group comprising 1 to 6 carbon atoms and wherein R' and R", which are identical or different, independently represent a linear or branched alkyl group comprising 1 to 6 carbon atoms or a phenyl group optionally substituted with at least one linear or branched alkyl group comprising 1 to 6 carbon atoms or wherein R' and R" represent together with the nitrogen atom to which they are bound a 5- to 7-membered ring which optionally comprises at least one other heteroatom selected from oxygen, sulphur, and nitrogen, said nitrogen being optionally substituted with an R'" group, which is a linear or branched alkyl group comprising 1 to 6 carbon atoms, or
an —$OCOR_9$ or —$OCOOR_9$ group, $R_9$ representing a linear or branched alkyl group comprising 1 to 6 carbon atoms, a cycloalkyl group comprising 3 to 6 carbon atoms, or a phenyl group optionally substituted with at least one substituent selected from the group consisting of:
a halogen,
a hydroxy,
a linear or branched alkyl group comprising 1 to 12 carbon atoms,
a linear or branched alkoxy group comprising 1 to 12 carbon atoms,
a haloalkyl or haloalkoxy group corresponding to the ($C_1$–$C_{12}$) alkyl or alkoxy groups above respectively which are substituted with at least one halogen atom,
a phenoxy or naphthoxy group optionally substituted with at least one linear or branched alkyl or alkoxy group comprising 1 to 12 carbon atoms, a linear or branched alkenyl group comprising 2 to 12 carbon atoms, an —NH$_2$ group, an —NHR group, R representing a linear or branched alkyl group comprising 1 to 6 carbon atoms, or a phenyl group optionally substituted with at least one linear or branched alkyl group comprising 1 to 6 carbon atoms, a

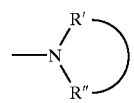

group, wherein R' and R", which are identical or different, independently represent a linear or branched alkyl group comprising 1 to 6 carbon atoms or a phenyl group optionally substituted with at least one linear or branched alkyl group comprising 1 to 6 carbon or wherein R'and R" represent together with the nitrogen atom to which they are bound a 5- to 7-membered ring which optionally comprises at least one other heteroatom selected from oxygen, sulphur, and nitrogen, said nitrogen being optionally substituted with an R'" group, which is a linear or branched alkyl group comprising 1 to 6 carbon atoms, and a methacryloyl group or an acryloyl group;

$R_5$, which are identical or different, represent, independently, the substituents listed above for the values of $R_4$ or at least two of the adjacent $R_5$ groups together form an aromatic or non-aromatic cyclic group having one or two annelated rings, optionally comprising at least one heteroatom selected from the group consisting of oxygen, sulphur, and nitrogen, this or these annelated rings being independently 5- to 7-membered aromatic or non-aromatic rings and being optionally substituted with at least one substituent selected from the group consisting of:

a halogen, a hydroxy, a linear or branched alkyl group comprising 1 to 12 carbon atoms, a linear or branched alkoxy group comprising 1 to 12 carbon atoms, a haloalkyl or haloalkoxy group corresponding to the ($C_1$–$C_{12}$) alkyl or alkoxy groups above respectively which are substituted with at least one halogen atom, a phenoxy or naphthoxy group optionally substituted with at least one linear or branched alkyl or alkoxy group comprising 1 to 12 carbon atoms, a linear or branched alkenyl group comprising 2 to 12 carbon atoms, an —NH$_2$ group, an —NHR group, R representing a linear or branched alkyl group comprising 1 to 6 carbon atoms, or a phenyl group optionally substituted with at least one linear or branched alkyl group comprising 1 to 6 carbon atoms, a

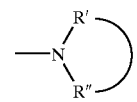

group, wherein R' and R", which are identical or different, independently represent a linear or branched alkyl group comprising 1 to 6 carbon atoms or a phenyl group optionally substituted with at least one linear or branched alkyl group comprising 1 to 6 carbon or wherein R' and R" represent together with the nitrogen atom to which they are bound a 5- to 7-membered ring which optionally comprises at least one other heteroatom selected from oxygen, sulphur, and nitrogen, said nitrogen being optionally substituted with an R'" group, which is a linear or branched alkyl group comprising 1 to 6 carbon atoms, and a methacryloyl group or an acryloyl group;

$R_6$, which are identical or different, represent, independently, a linear or branched alkyl group comprising 1 to 6 carbon atoms;

$R_7$ and $R_8$, which are identical or different, represent, independently, a hydrogen or a linear or branched alkyl group comprising 1 to 6 carbon atoms, or one of $R_7$ and $R_8$ represents a hydrogen or a linear or branched alkyl group comprising 1 to 6 carbon atoms and the other of $R_7$ and $R_8$ is selected from a hydroxy group, a linear or branched alkoxy group comprising 1 to 6 carbon atoms, and a —OCOR$_9$ or a —OCOOR$_9$ group, R$_9$ representing a linear or branched alkyl group comprising 1 to 6 carbon atoms or a cycloalkyl group comprising 3 to 6 carbon atoms or a phenyl group, optionally substituted with at least one substituent selected from the group consisting of:

a halogen, a hydroxy, a linear or branched alkyl group comprising 1 to 12 carbon atoms, a linear or branched alkoxy group comprising 1 to 12 carbon atoms, a haloalkyl or haloalkoxy group corresponding to the ($C_1$–$C_{12}$) alkyl or alkoxy groups above respectively which are substituted with at least one halogen atom, a phenoxy or naphthoxy group optionally substituted with at least one linear or branched alkyl or alkoxy group comprising 1 to 12 carbon atoms, a linear or branched alkenyl group comprising 2 to 12 carbon atoms, an —NH$_2$ group, an —NHR group, R representing a linear or branched alkyl group comprising 1 to 6 carbon atoms, or a phenyl group optionally substituted with at least one linear or branched alkyl group comprising 1 to 6 carbon atoms, a

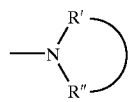

group, wherein R' and R", which are identical or different, independently represent a linear or branched alkyl group comprising 1 to 6 carbon atoms or a phenyl group optionally substituted with at least one linear or branched alkyl group comprising 1 to 6 carbon or wherein R' and R" represent together with the nitrogen atom to which they are bound a 5- to 7-membered ring which optionally comprises at least one other heteroatom selected from oxygen, sulphur, and nitrogen, said nitrogen being optionally substituted with an R'" group, which is a linear or branched alkyl group comprising 1 to 6 carbon atoms, and a methacryloyl group or an acryloyl group, or $R_7$ and $R_8$ together form an oxo group or a cycloalkyl group comprising 3 to 6 carbon atoms; and m is an integer from 0 to 3 and n and o are integers from 0 to 4.

2. A compound according to claim 1, wherein said compound is of formula (I) and wherein:

$R_1$ and $R_2$ are identical or different and independently represent optionally substituted aryl or heteroaryl groups, the basic structure of which is selected from the group consisting of phenyl, naphthyl, biphenyl, pyridyl, furyl, benzofuryl, dibenzofuryl, N—($C_1$–$C_6$) alkyl-carbazole, thienyl, benzothienyl, dibenzothienyl, and julolidinyl groups; or $R_1$ and $R_2$ together form an adamantyl or norbornyl group;

$R_4$ and $R_5$ represent a halogen, an alkyl group, or an alkoxy group; and m and n=1 and o=0.

3. A compound according to claim 1, wherein said compound is of formula (II) and wherein:

$R_1$ and $R_2$ are identical or different and independently represent optionally substituted aryl or heteroaryl groups, the basic structure of which is selected from the group consisting of phenyl, naphthyl, biphenyl, pyridyl, furyl, benzofuryl, dibenzofuryl, N—($C_1$–$C_6$) alkyl-carbazole, thienyl, benzothienyl, dibenzothienyl, and julolidinyl groups; or $R_1$ and $R_2$ together form an adamantyl or norbornyl group;

$R_4$ and $R_5$ represent a halogen, an alkyl group or an alkoxy group;

$R_7$ represents a hydroxy or an alkyl group, and $R_8$ represents a hydrogen or an alkyl group; and m and n=1.

4. A compound according to claim 1, wherein at least one of $R_1$ and $R_2$ represents a para-substituted phenyl group.

5. A method of preparing a compound according to claim 1, said comprising:

condensing an intermediate of formula (III) or (IV):

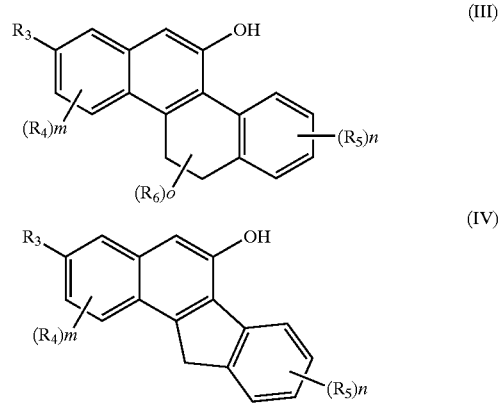

in which $R_3$, $R_4$, $R_5$, $R_6$, m, n, and o are as defined in claim 1, with a derivative of propargylic alcohol of formula (V):

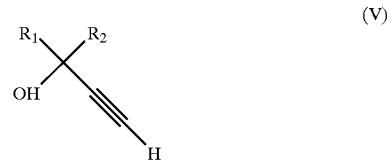

in which $R_1$ and $R_2$ are as defined in claim 1, the (III)/(V) or (IV)/(V) condensation being optionally carried out in the presence of a catalyst selected from the group consisting of para-toluenesulfonic acid, dodecylsulfonic acid, and bromoacetic acid; or with an aldehyde derivative of formula (V'):

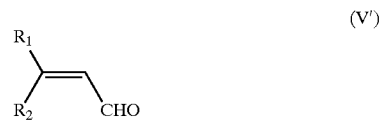

in which $R_1$ and $R_2$ are as defined in claim 1, the (III)/(V') or (IV)/(V') condensation being optionally carried out in the presence of a metallic complex of titanium.

6. A (co)polymer and/or reticulate obtained by polymerizing and/or cross-linking and/or grafting at least one monomer comprising at least one compound according to claim 1.

7. A photochromic compound which is constituted by a compound according to claim 1, or by a mixture of at least two compounds according to claim 1, or by a mixture of at least one compound according to claim 1 and at least one other photochromic compound of a different type and/or at least one non-photochromic coloring agent.

8. A photochromic composition which comprises:

at least one compound according to claim 1, and/or at least one linear or crosslinked (co)polymer which contains, in its structure, at least one compound according to claim 1, and optionally, at least one other photochromic compound of a different type and/or at least one non-photochromic coloring agent and/or at least one stabilizing agent.-

9. A (co)polymer matrix, characterized in that it comprises:
   at least one compound according to claim 1.

10. A (co)polymer matrix according to claim 9, wherein the (co)polymer is selected from the group consisting of:
   a (co)polymer obtained from an alkyl, cycloalkyl, (poly or oligo)ethylene glycol, aryl or arylalkyl mono-, di-, tri-, or tetra-acrylate or mono-, di-, tri-, or tetra-methacrylate which is optionally halogenated or which optionally comprises at least one ether and/or ester and/or carbonate and/or carbamate and/or thiocarbamate and/or urea and/or amide group,
   a polystyrene, polyether, polyester, polycarbonate, polycarbamate, polyepoxide, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate, or polyvinylbutyral,
   a (co)polymer obtained from a difunctional monomer of the following formula:

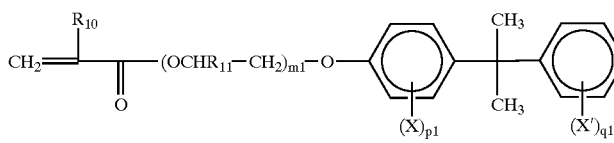

in which:
   $R_{10}$, $R'_{10}$, $R_{11}$, and $R'_{11}$ are identical or different and independently are a hydrogen or a methyl group,
   $m_1$ and $n_1$ independently are integers between 0 and 4 inclusive,
   X and X', which are identical or different, are a halogen, and
   $p_1$ and $q_1$ independently are integers between 0 and 4 inclusive;
   a copolymer of at least two types of copolymerizable monomers selected from the monomers which are precursors of the polymers listed above; and
   combinations thereof.

11. A (co)polymer matrix which comprises:
   at least one photochromic composition according to claim 8.

12. A (co)polymer matrix according to claim 11, wherein the (co)polymer is selected from the group consisting of:
   a (co)polymer obtained from an alkyl, cycloalkyl, (poly or oligo)ethylene glycol, aryl or arylalkyl mono-, di-, tri-, or tetra-acrylate or mono-, di-, tri-, or tetra-methacrylate which is optionally halogenated or which optionally comprises at least one ether and/or ester and/or carbonate and/or carbamate and/or thiocarbamate and/or urea and/or amide group,
   a polystyrene, polyether, polyester, polycarbonate, polycarbamate, polyepoxide, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate, or polyvinylbutyral,
   a (co)polymer obtained from a difunctional monomer of the following formula:

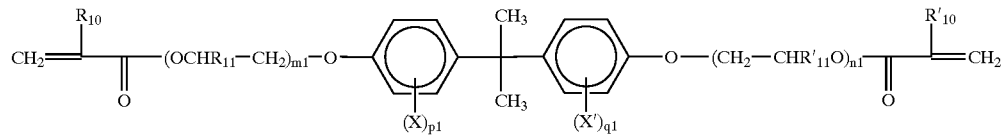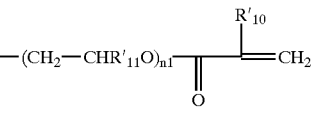

in which:
   $R_{10}$, $R'_{10}$, $R_{11}$ and $R'_{11}$ are identical or different and independently are a hydrogen or a methyl group,
   $m_1$ and $n_1$ independently are integers between 0 and 4 inclusive,
   X and X', which are identical or different, are a halogen, and
   $p_1$ and $q_1$ independently are integers between 0 and 4 inclusive;
   a copolymer of at least two types of copolymerizable monomers selected from the monomers which are precursors of the polymers listed above; and
   combinations thereof.

13. A (co)polymer matrix which comprises:
   at least one (co)polymer and/or reticulate according to claim 6.

14. A (co)polymer matrix according to claim 13, wherein the (co)polymer is selected from the group consisting of:
   a (co)polymer obtained from an alkyl, cycloalkyl, (poly or oligo)ethylene glycol, aryl or arylalkyl mono-, di-, tri-, or tetra-acrylate or mono-, di-, tri-, or tetra-methacrylate which is optionally halogenated or which optionally comprises at least one ether and/or ester and/or carbonate and/or carbamate and/or thiocarbamate and/or urea and/or amide group,
   a polystyrene, polyether, polyester, polycarbonate, polycarbamate, polyepoxide, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate, or polyvinylbutyral,
   a (co)polymer obtained from a difunctional monomer of the following formula:

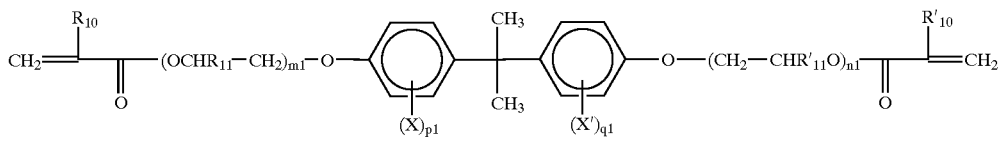

in which:

$R_{10}$, $R'_{10}$, $R_{11}$, and $R'_{11}$ are identical or different and independently are a hydrogen or a methyl group, $m_1$ and $n_1$ independently are integers between 0 and 4 inclusive, X and X', which are identical or different, are a halogen, and $p_1$ and $q_1$ independently are integers between 0 and 4 inclusive;

a copolymer of at least two types of copolymerizable monomers selected from the monomers which are precursors of the polymers listed above; and combinations thereof.

15. An ophthalmic or solar article comprising:

at least one compound according to claim 1.

16. An article according to claim 15, wherein said article is selected from the group consisting of a lens, a glazing, and an optical device.

17. An ophthalmic or solar article comprising:

at least one at least one photochromic composition according to claim 8.

18. An article according to claim 17, wherein said article is selected from the group consisting of a lens, a glazing, and an optical device.

19. An ophthalmic or solar article comprising:

at least one (co)polymer and/or reticulate according to claim 6.

20. An article according to claim 19, wherein said article is selected from the group consisting of a lens, glazing, and an optical device.

21. An ophthalmic or solar article comprising:

at least one matrix according to claim 9.

22. An article according to claim 21, wherein said article is selected from the group consisting of a lens, a glazing, and an optical device.

23. An ophthalmic or solar article comprising:

at least one matrix according to claim 11.

24. An article according to claim 23, wherein said article is selected from the group consisting of a lens, glazing, and an optical device.

25. An ophthalmic or solar article comprising:

at least one matrix according to claim 13.

26. An article according to claim 25, wherein said article is selected from the group consisting of a lens, a glazing, and an optical device.

* * * * *